United States Patent [19]

Ito et al.

[11] Patent Number: 5,068,381

[45] Date of Patent: Nov. 26, 1991

[54] POLY(SILVINYLENE)S AND A PROCESS FOR THEIR PREPARATION

[75] Inventors: Yoshihiko Ito; Masahiro Murakami, both of Kyoto, Japan

[73] Assignee: Shin-Etsu Chemical Co. Ltd., Tokyo, Japan

[21] Appl. No.: 667,266

[22] Filed: Mar. 11, 1991

[30] Foreign Application Priority Data

Mar. 13, 1990 [JP] Japan .................................. 1-62067

[51] Int. Cl.$^5$ .............................................. C07F 7/08
[52] U.S. Cl. .................................................. 556/431
[58] Field of Search ......................................... 556/431

[56] References Cited

U.S. PATENT DOCUMENTS

| | | | |
|---|---|---|---|
| 4,395,562 | 7/1983 | Yohji et al. | 556/431 |
| 4,921,989 | 5/1990 | Ishihara et al. | 556/431 |
| 5,001,247 | 3/1991 | Bortolin et al. | 556/431 |
| 5,011,961 | 4/1991 | Bortolin et al. | 556/431 |

*Primary Examiner*—Paul F. Shaver
*Attorney, Agent, or Firm*—Nixon & Vanderhye

[57] ABSTRACT

A process for preparing a poly(silvinylene) represented by the following general formula [III]:

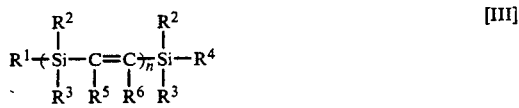

characterized in that (A) a polysilane represented by the following general formula [I]:

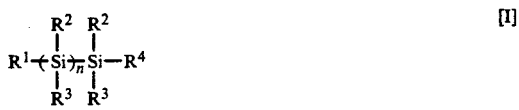

and (B) an acetylene represented by the following general formula [II]:

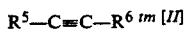

are reacted in the presence of a catalyst comprising an isocyanide compound and a palladium compound. This poly(silvinylene) is useful as a photosensitive material and a crosslinking agent. This poly(silvinylene) is obtained generally in high yield irrespective of the type of the substituent possessed by the silane that is a raw material.

3 Claims, No Drawings

POLY(SILVINYLENE)S AND A PROCESS FOR THEIR PREPARATION

BACKGROUND OF THE INVENTION

1. Field of the Invention

The present invention relates to a process for preparing poly(silvinylene)s and to poly(silvinylene)s having a novel structure that has vinyl groups each regularly introduced between the silicon atoms of adjacent Si-Si bonds.

2. Description of the Prior Art

The 1,2-addition reaction of a disilane to an acetylene bond is studied in detail using as a catalyst various transition metal complexes.

According to the above study, for example, in a disilane wherein a silicon atom is activated, for example, by an electron attractive group bonded to the silicon atom, when it is reacted with an acetylene compound, the 1,2-addition reaction proceeds preferentially to form an addition reaction product, but the yield is generally low.

For example, in the reaction between sym-tetramethyldisilane [HMe$_2$SiSiMe$_2$H] and dimethylacetylene dicarboxylate [MeOOC—C≡CCOOMe], the yield of dimethyl-α,α'-bis(dimethylsilyl) maleate, that is, the 1,2-adduct (formation of a cis-form), is 40%. In a similar reaction by phenylacetylene, a ring formation reaction proceeds preferentially over the addition reaction and while the yield of 1,1-dimethyl-3,4-diphenyl-1-silacyclopentadiene is 45%, the yield of cis-1,2-bis(dimethylsilyl)-1-phenylethylene, that is, the 1,2-adduct, is only 25%.

Further, it is pointed out that, in the reaction using a phosphine complex catalyst of nickel or platinum, the ring formation reaction is more preferential, and the principal product is a compound having a silacyclo ring [H. Okinoshima et al., J. Organomet. Chem. 86 C27-C30 (1975)].

Japanese Pre-examination Patent Publication (KOKAI) Nos. 88224/1979 and 88225/1979 disclose the preparation of cis-1,2-adduts by reacting a methyldichlorosilane with an acetylene in the presence of a palladium complex catalyst. However, in the case using a hexamethyldisilane, the yield is low as shown in the Comparative Examples.

That is, a process has not yet been found wherein a disilane whose substituents all are alkyl groups such as hexamethyldisilane is used to produce the 1,2-adduct for an acetylene type compound in high yield and a process capable of producing such a 1,2-adduct in generally high yield is desired.

A reaction for introducing regularly vinyl groups each between the silicon atoms of adjacent Si-Si bonds has not yet been known and such a compound has not been known.

SUMMARY OF THE INVENTION

Therefore, the object of the present invention is to provide a process capable of preparing a 1,2-adduct of an acetylene compound in high yield even from a polysilane whose substituents all are alkyl groups such as hexamethyldisilane and to provide poly(silvinylene)s having a novel structure that has vinyl groups each regularly introduced between the silicon atoms of adjacent Si-Si bonds.

According to the present invention, there is provided a process for preparing a poly(silvinylene) represented by the following general formula [III]:

wherein $R^1$, $R^2$, $R^3$, and $R^4$, which may be the same or different, each represent a member selected from the group consisting of a hydrogen atom, an alkyl group having 1 to 10 carbon atoms, an aryl group having 6 to 20 carbon atoms and an alkoxy group having 1 to 6 carbon atoms, $R^5$ and $R^6$, which may be the same, each represent a member selected from the group consisting of a hydrogen atom, an alkyl group having 1 to 10 carbon atoms, an aryl group having 6 to 20 carbon atoms, an alkoxycarbonyl group having 2 to 7 carbon atoms, and a trialkylsilyl group the alkyl groups of which have 1 to 10 carbon atoms, and n is an integer of 1 or over, for example, an integer of 1 to 6, characterized in that (A) a polysilane represented by the following general formula [I]:

wherein $R^1$, $R^2$, $R^3$, $R^4$, and n each have the same meaning as defined above, and (B) an acetylene represented by the following general formula 8 II]:

wherein $R^5$ and $R^6$ each have the same meaning as defined above, are reacted in the presence of a catalyst comprising an isocyanide compound and a palladium compound.

Out of the poly(silvinylene)s represented by the above general formula [III], those wherein n is 2 or over are novel substances.

Further, according to the present invention, there is provided a process for preparing a poly[α,β-bis(trialkylsilyl)vinylene] compound represented by the following general formula [V]:

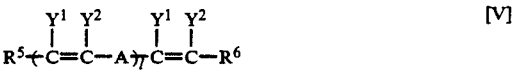

wherein $R^5$ and $R^6$ each have the same meaning as defined above, A represents an alkylene group represented by

in which a is an integer of 1 or over, for example, an integer of 1 to 6, a phenylene group or a vinylene group, l is an integer of 1 or over, for example, an integer of 1 to 3, $Y^1$ represents the following general formula:

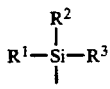

wherein $R^1$, $R^2$, and $R^3$ each have the same meaning as defined above, $Y^2$ represents the following general formula:

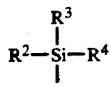

wherein $R^2$, $R^3$, and $R^4$ each have the same meaning as defined above, comprising the step of reacting, out of the polysilanes represented by the above general formula [I], particularly a disilane (A′) represented by the following general formula [Ia]:

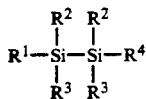 [Ia]

wherein $R^1$, $R^2$, $R^3$, and $R^4$ each have the same meaning as defined above, with a polyyne (C) represented by the following general formula [IV]:

$$R^5 + C \equiv C - A \overline{)_l} C \equiv C - R^6 \quad [IV]$$

wherein $R^5$, $R^6$, A, and l each have the same meaning as defined above, in the presence of a catalyst comprising an isocyanide and a palladium compound.

According to the present invention, poly(silvinylene)s having a novel structure that has vinyl groups each regularly introduced between the silicon atoms of all adjacent Si—Si bonds can be obtained and such poly(silvinylene)s are useful industrially, for example, as a photosensitive material and a crosslinking agent.

Further, according to the present invention, such poly(silvinylene)s are obtained generally in high yield regardless of the type of the substituents possessed by the silane used as a raw material.

DETAILED DESCRIPTION OF PREFERRED EMBODIMENTS

Preparation of Poly(silvinylene)s

In the present process for preparing a poly(silvinylene), the synthesis reaction is represented by the following equation:

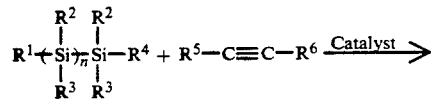

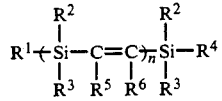

Reactants

Polysilanes used as a reactant for the above reaction are those represented by the above general formula [I] wherein $R^1$, $R^2$, $R^3$, and $R^4$ each represents a member selected from the group consisting of a hydrogen, an alkyl group such as a methyl group, an ethyl group, a propyl group, and a butyl group, an aryl group such as a phenyl group, a naphthyl group, and a substituted phenyl group, and an alkoxy group such as a methoxy group and an ethoxy group. These $R^1$, $R^2$, $R^3$, and $R^4$ may be the same or different and preferably each represent a methyl group or a phenyl group in view of readiness of the availability of the raw material and readiness of the synthesis.

As the polysilane compounds, specifically, for example, $Me_3SiSiMe_3$, $Me_3PhSiSiMe_3$, $PhMe_2SiSiMe_2Ph$, $(MeO)Me_2SiSIMe_2(MeO)$, $Me_3SiSi(Me_2)SiMe_3$, $Me_3SiSi(Me_2)SiMe_2(t\text{-}Bu)$, $Me_3SiSi(Me_2)SiMe_2Ph$, $Me_3Si(SiMe_2)_2SiMe_3$, and $Me_3Si(SiMe_2)_3SiMe_3$ can be exemplified. Herein, Me stands for a methyl group, t-Bu stands for a tertiary butyl group, and Ph stands for a phenyl group, the same being applied hereinafter.

The other reactant, i.e., acetylenes are those represented by the above general formula [II] wherein $R^5$ and $R^6$ each represent a member selected from the group consisting of a hydrogen atom, an alkyl group such as amethyl group, an ethyl group, a propyl group, and a butyl group, an aryl group such as a phenyl group, an alkoxycarbonyl group such as a methoxycarbonyl group, and a trialkylsilyl group such as a trimethylsilyl group.

As the acetylene compounds, specifically, for example, $CH \equiv CH$, $n\text{-}C_4H_9C \equiv CH$, $n\text{-}C_6H_{13}C \equiv CH$, $PhC \equiv CH$, $H_3COOCC \equiv CCOOCH_3$, and $(CH_3)_3SiC \equiv CH$ can be mentioned.

Catalysts

In the present invention, in the reaction between the polysilane and the acetylene, a mixed catalyst comprising an isocyanide and a palladium compound is used.

Although, as the isocyanide, an aromatic isonitrile such as 2,6-xylylisocyanide and 2,6-diisopropylphenylisocyanide, or an alkylisocyanide such as primary to tertiary alkylisocyanides can be used, preferably a tertiary alkylisocyanide such as tertiary butylisocyanide, di(t-butyl)isocyanide, 1,1,3,3-tetramethylbutylisocyanide (t-octylisocyanide), and 1-adamantylisocyanide is used.

Although there is no particular restriction on the palladium compound, palladium compounds which can be apt to be reduced from the bivalence to the zero valence or whose valence is zero are desirable and, for example, palladium(II) acetate, cyclopentadienyl$\pi$allylpalladium, tetrakis(triphenylphosphine)palladium, or diacetoxybis(triphenylphosphine)palladium is preferably used.

In the mixed catalyst, desirably the isocyanide is used in such a proportion that the molar amount is 15 to 50 times as much as that of the palladium compound and preferably the mixed catalyst is used in a proportion of 10 to 40 mol % for the reactant.

Synthesis Reaction

The reaction between the polysilane and the acetylene is preferably carried out under an atmosphere of an inert gas such as a nitrogen using an inactive solvent such as toluene and the reaction temperature is generally in the range of 80° to 150 °C.

When a gas such as acetylene is used as a reactant, it is efficient to carry out the reaction under pressure.

After the completion of the reaction, per se known refining procedures such as distillation and recrystallization are carried out to obtain the aimed poly(silvinylene).

Incidentally, in the above synthesis reaction, although the reaction between hexamethyldisilane and an acetylene produces the cis-form as generally known, when acetylene gas is used as an acetylene and the reaction temperature is too high or the reaction temperature is too long, isomerization to the trans-form takes place, which is not particularly beneficial.

Poly(silvinylene)s

The thus obtained poly(silvinylene) is represented by the above general formula [III]. Typical examples of the present poly(silvinylene) are shown below, which are not meant to restrict the present invention.

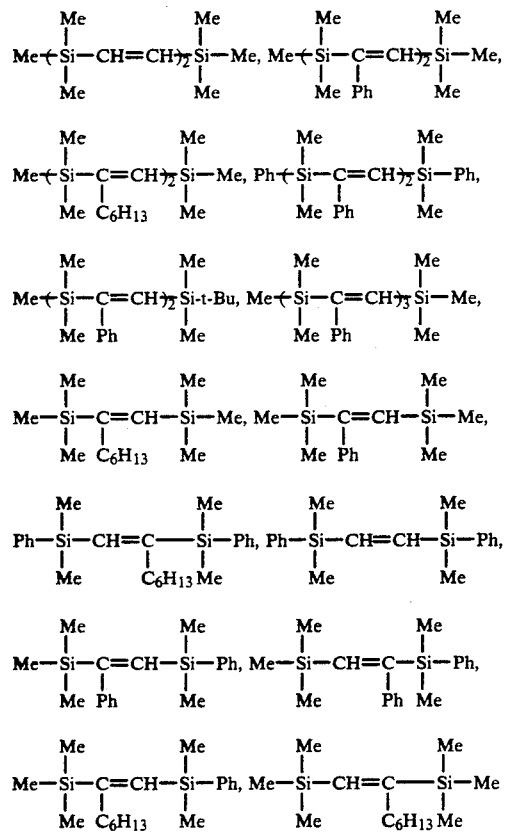

The above poly(silvinylene)s are compounds useful as a photosensitive material and a crosslinking agent and, out of them, those wherein n is 2 or over are novel substances.

Preparation of poly[α,β-bis(trialkylsilyl)vinylene] compounds

In the present invention, when, out of the polysilane represented by the above general formula [I], particularly the disilane represented by the above general formula [Ia] is reacted with the polyyne represented by the above general formula [IV], a poly[α,β-bis(trialkylsilyl)vinylene] compound can be obtained in high yield.

The disilane used herein is represented by the above general formula [Ia], that is, by

wherein $R^1$, $R^2$, $R^3$, and $R^4$ each have the same meaning as defined above, and as $R^1$, $R^2$, $R^3$, and $R^4$, those exemplified in the above general formula [I] can be mentioned.

The polyyne is represented by the above general formula [IV], that is, by

wherein $R^5$, $R^6$, and A have the same meaning as defined above. Specific examples of $R^5$ and $R^6$ are as exemplified in respect of the above general formula [II]. Examples of A include, for example, an alkylene group such as methylene, dimethylene, trimethylene and tetremethylene, a phenylene group and a vinylene group. Specific examples of the polyyne that are preferably used include 1,5-hexadiyne, 1,7-ocatadiyne, and H(C≡C—CH$_2$CH$_2$)$_2$C≡CH.

The reaction of the disilane with the polyyne is carried out by using a mixed catalyst of an isocyanide and a palladium compound in a similar manner to the synthesis of the above poly(silvinylene)s and the reaction conditions and the like are the same as those of the synthesis of the poly(silvinylene)s.

Thus, poly[α,β-bis(trialkylsilyl)vinylene] compounds represented by the above general formula [V], that is, by

wherein $R^5$, $R^6$, A, and l each have the same meaning as defined above, $Y^1$ represents the following general formula:

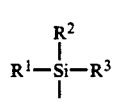

wherein $R^1$, $R^2$, and $R^3$ each have the same meaning as defined above, and $Y^2$ represents the following general formula:

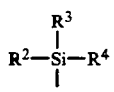

wherein R², R³, and R⁴ each have the same meaning as defined above, are produced.

A typical example of the poly[α,β-bis(trialkylsilyl)vinylene] below, which is not meant to restrict the present invention:

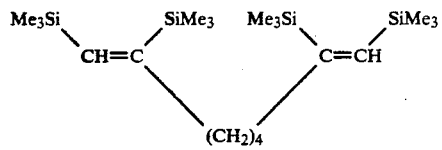

EXAMPLES

Example 1

Palladium acetate (0.1 mmol), t-octylisocyanide (4.0 mmol), octamethyltrisilane (5.0 mmol), and toluene (5 mmol) were charged into a 250-ml steel cylinder and acetylene gas was sealed into the cylinder until the pressure reached 30 kg/cm².

Then it was heated to 110° C. and the reaction was continued for 13 hours. Then the reaction mixture was distilled and the compound given below was obtained in a yield of 73%. The results of the NMR and the elemental analysis are also given below.

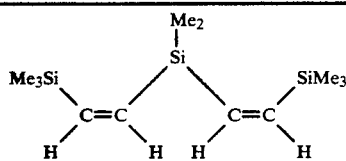

¹H-NMR: (CDCl₃)
δ (ppm)

0.108 (s, 18H)
0.251 (s, 6H)
6.815 (m, 2H)
6.807 (m, 2H)

| Elemental analysis: (%) | | | |
|---|---|---|---|
| | C | H | Si |
| Calculated | 56.17 | 11.00 | 32.83 |
| Found | 56.23 | 10.97 | 32.89 |

Example 2

A mixed solution of palladium acetate (0.1 mmol), t-octylisocyanide (1.5 mmol), octamethyltrisilane (5.0 mmol), phenylacetylene (20 mmol), and toluene (5 mmol) was reacted for 6 hours with stirring while refluxing the toluene moderately.

After the completion of the reaction, the reaction solution was passed through a silica gel column (the filled silica gel: 100–200 mesh, FLORISIL (tradename) supplied by Wako Junyaku Kogyo K.K.) previously treated with triethylamine and was washed with hexane to remove the catalyst. Then the hexane solution was condensed, the resulting viscous solution was dissolved in hexane again, the solution was kept at a low temperature (−50° C.), and the solid crystals were separated to obtain a compound consisting of three isomers ((a), (b), and (c)) given below in a yield of 95%. The proportion of the isomers (a), (b), and (c) is 3:4:2. The results of the NMR and the elemental analysis are also shown below.

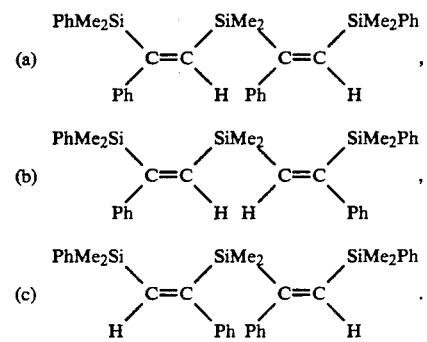

| ¹H-NMR: (CDCl₃) | | |
|---|---|---|
| (a) | (b) | (c) |
| δ (ppm) 0.082 (s, 9H) | 0.128 (s, 18H) | 0.136 (s, 18H) |
| 0.180 (s, 9H) | | 0.366 (s, 6H) |
| 0.343 (s, 6H) | 0.413 (s, 6H) | |
| 6.468 (s, 1H) | 6.375 (s, 2H) | 6.561 (s, 2H) |
| 6.561 (s, 1H) | | |
| 6.8 to 7.3 (m, 10H) | 6.8 to 7.3 (m, 10H) | 6.8 to 7.3 (m, 10H) |

| Elemental analysis: (%) | | | |
|---|---|---|---|
| | C | H | Si |
| Calculated | 70.51 | 8.88 | 20.61 |
| Found | 70.55 | 8.87 | 20.64 |

Example 3

Example 2 was repeated, except that, in place of octamethyltrisilane, 1,3-diphenyl-1,1,2,2,3,3-hexatrimethylsilane (5.0 mmol) was used and the reaction time was 7.5 hours, thereby preparing a compound consisting of the following three isomers ((a), (b), and (c)) in a yield of 88%. The proportion of the isomers (a), (b), and (c) was 36:33:31.

(a) PhMe₂Si\C=C/SiMe₂\C=C/SiMe₂Ph, Ph/ \H Ph/ \H (b) PhMe₂Si\C=C/SiMe₂\C=C/SiMe₂Ph, Ph/ \H H/ \Ph (c) PhMe₂Si\C=C/SiMe₂\C=C/SiMe₂Ph. H/ \Ph Ph/ \H

Example 4

Example 2 was repeated, except that, in place of phenylacetylene, 1-octyne (20 mmol) was used and the reaction time was 4 hours, thereby preparing a compound consisting of the following three isomers ((a), (b), and (c)) in a yield of 62%. The proportion of the isomers (a), (b), and (c) was 6:4:1.

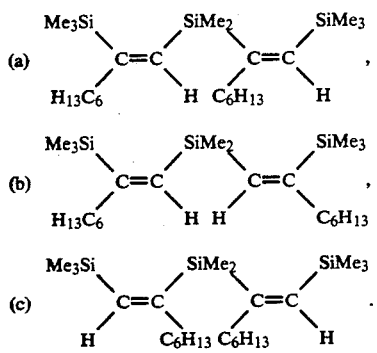

Example 5

Example 2 was repeated, except that, in place of octamehyltrisilane, 1-t-butyl-1,1,2,2,3,3,3-heptatrimethylsilane (5.0 mmol) was used and the reaction time was 5 hours, thereby preparing a compound consisting of the following four isomers ((a), (b), (c), and (d)) in a yield of 92%. The proportion of the isomers (a), (b), (c), and (d) was 36:33:31:16.

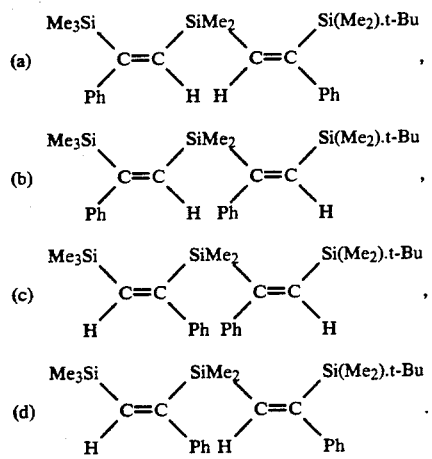

Example 6

A mixed solution of palladium acetate (0.1 mmol), t-octylisocyanide (4.0 mmol), decamethyltetrasilane (5.0 mmol), phenylacetylene (30 mmol), and toluene (5 ml) was kept at 80° C. for 4 hours to allow the reaction to proceed.

After the completion of the reaction, the same treatment as that in Example 2 was carried out to obtain the following compound in a yield of 47%. The results of the NMR and the elemental analysis are also given below.

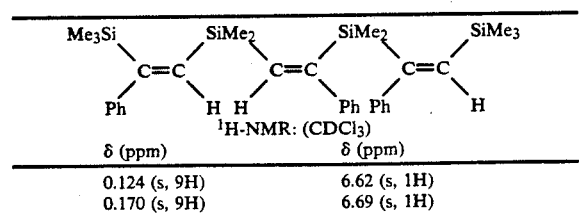

$^1$H-NMR: (CDCl$_3$)

| δ (ppm) | δ (ppm) |
|---|---|
| 0.124 (s, 9H) | 6.62 (s, 1H) |
| 0.170 (s, 9H) | 6.69 (s, 1H) |
| 0.439 (s, 12H) | 6.92 |
| 6.58 (s, 1H) | to 7.35 (m, 15H) |

Elemental analysis: (%)

|  | C | H | Si |
|---|---|---|---|
| Calculated | 71.76 | 8.50 | 19.74 |
| Found | 71.73 | 8.49 | 19.77 |

Example 7

(1) A mixed solution of palladium acetate (0.1 mmol), t-butylisocyanide (5.0 mmol), hexamethyldisilane (5.0 mmol), 1-octyne (7.5 mmol), and toluene (5 ml) was reacted for 6 hours with stirring while refluxing the toluene moderately.

After the completion of the reaction, distillation for refining was carried out to obtain cis-1,2-bis(trimethylsilyl)-1-octene represented by the formula given below in a yield of 62%. The results of the NMR are also given below.

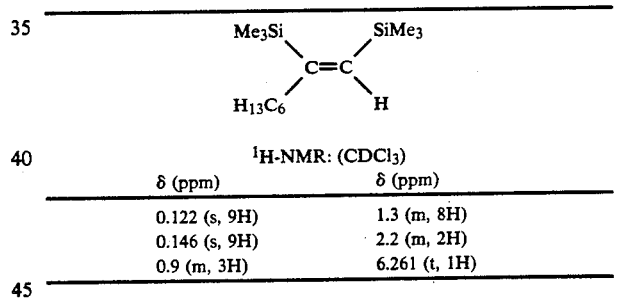

$^1$H-NMR: (CDCl$_3$)

| δ (ppm) | δ (ppm) |
|---|---|
| 0.122 (s, 9H) | 1.3 (m, 8H) |
| 0.146 (s, 9H) | 2.2 (m, 2H) |
| 0.9 (m, 3H) | 6.261 (t, 1H) |

(2) A mixed solution of palladium acetate (0.1 mmol), t-octylisocyanide (1.5 mmol), hexamethyldisilane (5.0 mmol), 1-octyne (7.5 mmol), and toluene (5 ml) was reacted for 6 hours with stirring while refluxing the toluene moderately.

After the completion of the reaction, distillation for refining was carried out to obtain cis-1,2-bis(trimethylsilyl)-1-octene in a yield of 75%.

Example 8

A mixed solution of palladium acetate (0.1 mmol), t-butylisocyanide (1.5 mmol), hexamethyldisilane (5.0 mmol), phenylacetylene (6.0 mmol), and toluene (5 ml) was reacted for 7 hours with stirring while refluxing the toluene moderately.

After the completion of the reaction, distillation for refining was carried out to obtain cis-1,2-bis(trimethylsilyl)-1-phenylethylene represented by the formula given below in a yield of 74%. The results of the NMR are also given below.

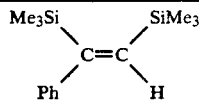

¹H-NMR: (CDCl₃)
δ (ppm)

0.149 (s, 9H)
0.208 (s, 9H)
6.425 (s, 1H)
7.0 to 7.3 (m, 5H)

Example 9

A mixed solution of palladium acetate (0.1 mmol), t-butylisocyanide (1.5 mmol), hexamethyldisilane (5.0 mmol), methyl acetylenecarboxylate (5.0 mmol), and toluene (5 ml) was reacted for 36 hours with stirring while refluxing the toluene moderately.

After the completion of the reaction, distillation for refining was carried out to obtain cis-1,2-bis(trimethylsilyl)-1,2-dicarboxyethylene represented by the formula given below in a yield of 46%. The results of the NMR are also given below.

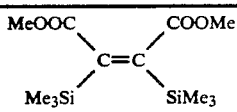

¹H-NMR: (CDCl₃)
δ (ppm)

0.239 (s, 18H)
3.677 (s, 6H)

Example 10

A mixed solution of palladium acetate (0.1 mmol), t-octylisocyanide (1.5 mmol), 1,2-diphenyl-1,1,2,2-tetramethyldisilane (5.0 mmol), 1-octyne (7.5 mmol), and toluene (5 ml) was reacted for 4.5 hours with stirring while refluxing the toluene moderately.

After the completion of the reaction, distillation for refining was carried out to obtain cis-1,2-bis(phenyldimethylsilyl)-1-octene represented by the formula given below in a yield of 96%. The results of the NMR are also given below.

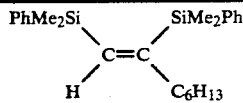

| ¹H-NMR: (CDCl₃) | |
|---|---|
| δ (ppm) | δ (ppm) |
| 0.168 (s, 6H) | 1.3 (m, 8H) |
| 0.265 (s, 6H) | 2.2 (m, 2H) |
| 0.9 (m, 3H) | 7.2 to 7.5 (m, 10H) |

Example 11

Palladium acetate (0.1 mmol), t-octylisocyanide (4.0 mmol), 1,1,2,2-tetramethyldisilane (5.0 mmol), and toluene (5 mmol) were charged into a 250-ml steel cylinder and acetylene gas was sealed into the cylinder until the pressure reached 30 kg/cm².

Then it was heated to 110° C. and the reaction was continued for 13 hours. Then the reaction product was distilled and cis-1,2-bis(phenyldimethylsilyl)-ethylene represented by the formula given below was obtained in a yield of 73%. The results of the NMR are also given below.

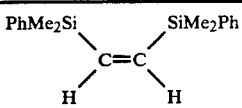

¹H-NMR: (CDCl₃)
δ (ppm)

0.236 (s, 12H)
7.039 (s, 2H)
7.3 to 7.6 (m, 10H)

Example 10

A mixed solution of palladium acetate (0.1 mmol), t-octylisocyanide (4.0 mmol), 1-phenyl-1,1,2,2,2-pentamethyldisilane (5.0 mmol), phenylacetylene (7.5 mmol), and toluene (5 ml) was reacted for 4 hours with stirring while refluxing the toluene moderately.

After the completion of the reaction, by carrying out the same treatment as that of Example 2, a compound consisting of the following two isomers ((a) and (b)) was obtained in a yield of 86%. The proportion of the isomers (a) and (b) was 8:2.

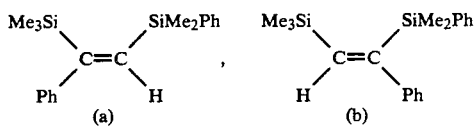

Example 13

Example 12 was repeated, except that, in place of phenylacetylene, 1-octyne (7.5 mmol) was used and the reaction was continued for 3.5 hours, thereby obtaining a product consisting of the following two isomers ((a) and (b)) in an yield of 79%. The proportion of the isomers (a) and (b) was 7:3.

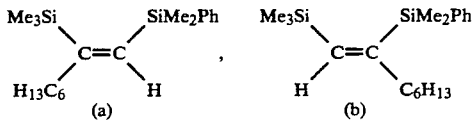

Example 14

Example 8 was repeated, except that, in place of phenylacetylene, 1,7-octadiyne (2.0 mmol) was used and the reaction was continued for 11 hours, thereby obtaining cis-1,2-cis-7,8-tetrakis(trimethylsilyl)-1,7-octadiene represented by the formula given below in a yield of 46%. The results of the NMR are also given below.

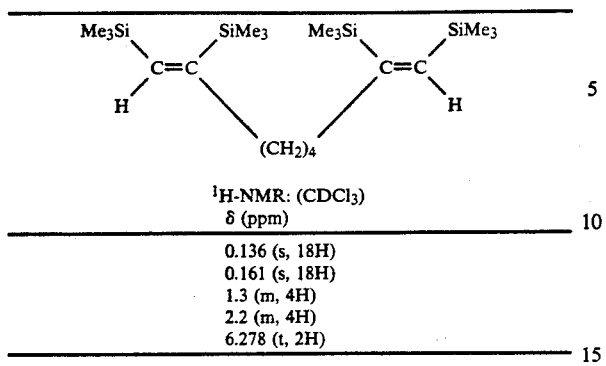

| $^1$H-NMR: (CDCl$_3$) |
| --- |
| δ (ppm) |
| 0.136 (s, 18H) |
| 0.161 (s, 18H) |
| 1.3 (m, 4H) |
| 2.2 (m, 4H) |
| 6.278 (t, 2H) |

We claim:

1. A process for preparing a poly(silvinylene) represented by the following general formula [III]:

wherein R$^1$, R$^2$, R$^3$, and R$^4$, which may be the same or different, each represent a member selected from the group consisting of a hydrogen atom, an alkyl group having 1 to 10 carbon atoms, an aryl group having 6 to 20 carbon atoms and an alkoxy group having 1 to 6 carbon atoms, R$^5$ and R$^6$, which may be the same, each represent a member selected from the group consisting of a hydrogen atom, an alkyl group having 1 to 10 carbon atoms, an aryl group having 6 to 20 carbon atoms, an alkoxycarbonyl group having 2 to 7 carbon atoms, and a trialkylsilyl group the alkyl groups of which have 1 to 10 carbon atoms, and n is an integer characterized in that (A) a polysilane represented by the following general formula [I]:

wherein R$^1$, R$^2$, R$^3$, R$^4$, and n each have the same meaning as defined above, and (B) an acetylene represented by the following general formula [II]:

$$R^5—C\equiv C—R^6 \quad [II]$$

wherein R$^5$ and R$^6$ each have the same meaning as defined above, are reacted in the presence of a catalyst comprising an isocyanide compound and a palladium compound.

2. A process for preparing a poly [α,β-bis(trialkylsily)vinylene] compound represented by the following general formula [V]:

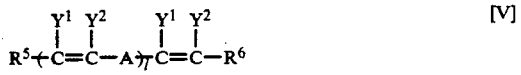

wherein R$^5$ and R$^6$ each have the same meaning as defined above, A represents an alkylene group represented by $$+CH_2\,\overline{\jmath_a}$$

in which a is an integer of 1 or over, a phenylene group or a vinylene group, 1 is an integer of 1 or over, Y$^1$ represents the following general formula:

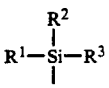

wherein R$^1$, R$^2$, and R$^3$, which may be the same or different, each represent a member selected from the group consisting of a hydrogen atom, an alkyl group having 1 to 10 carbon atoms, an aryl group having 6 to 20 carbon atoms and an alkoxy group having 1 to 6 carbon atoms, and Y$^2$ represents the following general formula:

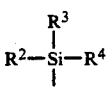

wherein R$^2$, R$^3$, and R$^4$, which may be the same or different, each represent a member selected from the group consisting of a hydrogen atom, an alkyl group having 1 to 10 carbon atoms, an aryl group having 6 to 20 carbon atoms and an alkoxy group having 1 to 6 carbon atoms, characterized in that (A') a disilane represented by the following general formula [Ia]:

wherein R$^1$, R$^2$, R$^3$, and R$^4$ each have the same meaning as defined above, and (C) a polyyne represented by the following general formula [IV]:

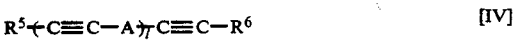

wherein R$^5$ and R$^6$, which may be the same or different, each represent a member selected from a group consisting of a hydrogen atom, an alkyl group having 1 to 10 carbon atoms, an aryl group having 6 to 20 carbon atoms, an alkoxycarbonyl group having 2 to 7 carbon atoms, and a trialkylsilyl group and A and 1 each have the same meaning as defined above, are reacted in the presence of a catalyst comprising an isocyanide and a palladium compound.

3. A poly(silvinylene) represented by the above formula [III], in claim 1 wherein n is an integer of 2 or over.

* * * * *

UNITED STATES PATENT AND TRADEMARK OFFICE
CERTIFICATE OF CORRECTION

PATENT NO. : 5,068,381

DATED : November 26, 1991

INVENTOR(S) : ITO et al

It is certified that error appears in the above-identified patent and that said Letters Patent is hereby corrected as shown below:

On Title Page: Column 1, Item [30] last line change "1-62067" to --2-62067--.

Signed and Sealed this

Thirtieth Day of November, 1993

Attest:

BRUCE LEHMAN

Attesting Officer

Commissioner of Patents and Trademarks